United States Patent [19]

Don Michael

[11] Patent Number: 5,222,941

[45] Date of Patent: Jun. 29, 1993

[54] METHOD OF DISSOLVING AN OBSTRUCTION IN A VESSEL

[76] Inventor: T. Anthony Don Michael, 309 Panorama Dr., Bakersfield, Calif. 93305

[21] Appl. No.: 808,924

[22] Filed: Dec. 18, 1991

Related U.S. Application Data

[60] Division of Ser. No. 492,582, Mar. 13, 1990, Pat. No. 5,090,960, which is a continuation-in-part of Ser. No. 464,029, Jan. 12, 1990, abandoned.

[51] Int. Cl.⁵ .............................................. A61M 29/00
[52] U.S. Cl. .................................... 604/101; 128/632; 606/194; 604/28
[58] Field of Search ................................ 604/96-101, 604/21, 27, 28; 606/191, 192, 194; 128/633, 634, 632

[56] References Cited

U.S. PATENT DOCUMENTS

| | | | |
|---|---|---|---|
| 4,512,348 | 4/1985 | Uchigaki et al. | 128/632 |
| 4,610,662 | 9/1986 | Weikl et al. | 604/101 |
| 4,696,668 | 9/1987 | Wilcox | 604/101 |
| 4,705,503 | 11/1987 | Dorman et al. | 128/632 |
| 4,824,436 | 4/1989 | Wolinsky | 604/101 |
| 4,944,745 | 7/1990 | Sogard et al. | 604/96 |
| 4,983,167 | 1/1991 | Sahota | 604/96 |
| 5,000,734 | 3/1991 | Boussignac et al. | 604/96 |
| 5,020,537 | 6/1991 | Günther | 128/634 |
| 5,028,395 | 7/1991 | Sebille et al. | 128/634 |
| 5,047,208 | 9/1991 | Schweitzer et al. | 128/634 |
| 5,059,178 | 10/1991 | Ya | 604/101 |
| 5,078,135 | 1/1992 | Capnoli | 128/632 |
| 5,097,834 | 3/1992 | Skrabal | 128/632 |
| 5,109,850 | 5/1992 | Blanco et al. | 128/635 |

Primary Examiner—C. Fred Rosenbaum
Assistant Examiner—Chalin Smith
Attorney, Agent, or Firm—Spensley Horn Jubas & Lubitz

[57] ABSTRACT

A method of dissolving an obstruction in a blood vessel by the steps of preventing blood which is in contact with the obstruction from flowing through the vessel to locations downstream of the obstruction while permitting blood to flow through a passage past the obstruction; delivering to the obstruction a dissolution agent which works in conjunction with blood components to effect dissolution of the obstruction; analyzing the composition of fluid in contact with the obstruction; and at least periodically supplying blood to the fluid in contact with the obstruction, based on the result of the analyzing step.

6 Claims, 3 Drawing Sheets

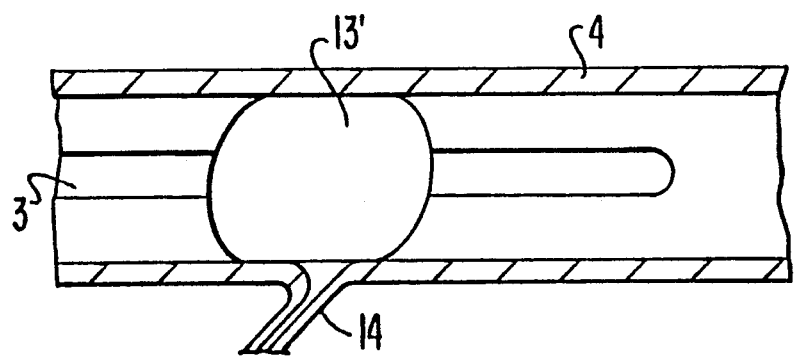

METHOD OF DISSOLVING AN OBSTRUCTION IN A VESSEL

CROSS REFERENCE TO RELATED APPLICATIONS

This is a division of U.S. application Ser. No. 07/492,582 filed Mar. 13, 1990 now U.S. Pat. No. 5,090,960, itself a continuation-in-part of U.S. application Ser. No. 07/464,029 filed Jan. 12, 1990, now abandoned.

BACKGROUND OF THE INVENTION

The present invention relates to the treatment of obstructions in a blood vessel, and particularly the elimination of such obstructions by chemical dissolution.

The formation of a blood clot in the cardiovascular system usually requires prompt medical intervention, and this is particularly true in the case of arterial blood clots, most particularly those in a coronary artery, since such clots can be life threatening. Obstructions formed of other materials, such as plaque and fibrin, can also require medical intervention.

Various techniques for removing such obstructions are known, these techniques generally involving surgical intervention or the delivery of a dissolution agent, e.g., a thrombolytic agent.

In principle, the use of a thrombolytic agent offers the advantage of avoiding the physical trauma associated with surgical intervention. However, the techniques typically employed to deliver thrombolytic agent to the site of a clot are somewhat complex and/or require the introduction of a considerable quantity of thrombolytic agent into the blood stream in view of the fact that such agent is entrained in the blood stream and thus carried away from the site of the clot, unless the clot is completely blocking the vessel. Since thrombolytic agents are foreign substances to the patient's body, the larger the quantity of such agent introduced into the blood stream, the greater the danger of adverse side effects and the greater the cost. In addition, if large quantities of agent are introduced into the blood stream, the result could be that subsequent surgical intervention which might otherwise be indicated could not be performed. Similar considerations apply to other types of dissolution agents.

U.S. Pat. No. 4,423,725, which issued to O. E. Baran on Jan. 3, 1984, describes an intervention device composed of a catheter having a blood flow lumen, a chemical delivery lumen and a suction lumen, associated with two annular cuffs which are inflatable to isolate a blood vessel region containing an obstruction. This patent discloses the treatment of blood vessel obstructions by balloon angioplasty followed by the application of anticoagulant drugs or cholesterol diluting drugs.

SUMMARY OF THE INVENTION

It is therefore an object of the present invention to dissolve obstructions in a blood vessel in a minimum of time and while introducing a minimum of dissolution agent into the blood vessel.

Another object of the invention is to effect dissolution by a simple and readily controllable procedure which allows, particularly, control of the relative concentrations of dissolution agent and blood at the treatment site.

Still another object of the invention is to permit reliable verification that the dissolution agent is being delivered precisely to the site of the clot.

Yet another object of the invention is to facilitate the delivery an X-ray detectable dye to the clot site.

The above and other objects are achieved, according to the present invention, by a device for performing regional perfusion obstruction dissolution, comprising:

an infusion catheter insertable into a blood vessel to extend across the site of a clot, the infusion catheter having a length and extending in the direction of the length between a distal end via which the infusion catheter is inserted into the blood vessel and a proximal end remote from the distal end, and the infusion catheter being configured to have:

first flow means defining a blood bypass flow path extending along a portion of the length of the infusion catheter and communicating with regions surrounding the infusion catheter at first and second locations along the length of the infusion catheter such that when the infusion catheter extends across an obstruction site in a blood vessel, the first and second locations are positioned upstream and downstream, respectively, of the obstruction with respect to the direction of blood flow in the vessel; and second flow means defining a dissolution agent flow path extending along the length of the infusion catheter from the proximal end and communicating with a region surrounding the infusion catheter at a third location along the length of the infusion catheter between the first and second locations for delivering dissolution agent to the obstruction when the infusion catheter extends across the obstruction site in the blood vessel;

a suction catheter insertable into the blood vessel and positionable at the obstruction site independently of the infusion catheter and having proximal and distal ends and a suction lumen extending between the proximal and distal ends;

first blocking means carried by the infusion catheter at a fourth location between the first and second locations and spaced from the third location to be located at one side of the obstruction site when the infusion catheter is inserted into the blood vessel; and second blocking means carried by one of the catheters at a position to be located at the other side of the obstruction site at least when both of the catheters are positioned at the obstruction site; wherein both of the blocking means are controllable for blocking blood flow through the vessel along a path exterior to the catheters.

The objects according to the invention are further achieved by using the device defined above in the following manner:

introducing the catheters into a blood vessel containing an obstruction in a manner such that the obstruction is between the first and second blocking means, and the third location is located in proximity to the obstruction;

causing the blocking means to block blood flow around the catheters while blood continues to flow through the blood bypass flow path; and delivering a dissolution agent to the obstruction via the dissolution agent flow path.

The device according to the invention will be described with reference to clot dissolution but could also be employed to deliver a plaque dissolving or fibrin dissolving substance to a blockage or obstruction.

BRIEF DESCRIPTION OF THE DRAWINGS

FIG. 7 is a side view similar to FIG. 1 showing a modified form of one component of a device according to the invention.

DESCRIPTION OF THE PREFERRED EMBODIMENTS

Figure 1:
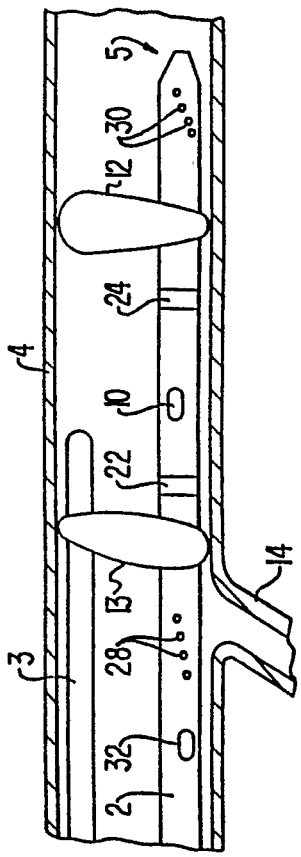
FIG. 1 is a side view of a first embodiment of a device according to the present invention.

In order to dissolve a clot, for example, it is necessary to bring a suitable clot dissolution, or thrombolytic, agent into contact with the clot, one substance which presently finds wide use being urokinase. Referring to FIG. 1, in order to deliver such agent to the clot site, catheter 2 is provided with an axial lumen 8 (FIG. 3) whose distal end terminates in a comparatively large outlet opening 10. The proximal end of lumen 8 (not shown) would extend outside of the patient's body and be connected to a suitable source of the dissolution agent.

Good medical practice generally dictates that the quantity of any foreign substance introduced into a patient's body be no more than that required to produce the intended result, whereby side effects can be prevented or at least minimized. In order to minimize the quantity of clot dissolution agent employed to remove a clot, the device according to the present invention will serve to block the blood vessel at a location downstream of the clot so that the dissolution agent introduced via lumen 8 and outlet opening 10 will be confined to the region of the clot. Since the dissolution agent will be substantially prevented from flowing away from the clot site, it will be appreciated that this arrangement allows the quantity of substance introduced into the body to be maintained at the minimum amount needed to produce the desired result.

A more specific goal of the present invention is to efficiently eliminate clots or other obstructing materials by the action of a dissolution agent which works in conjunction with certain blood components, e.g., enzymes, to effect dissolution.

The speed of the dissolving action is influenced by the quantitative relation between the dissolution agent and the cooperating blood component and a given dissolution reaction will be optimized by maintaining this relation in a given range. According to this invention, optimization can be achieved by controlling the flow rate of dissolution agent to the clot site, controlling the quantity of blood at the clot site, and monitoring the resulting chemical composition at the clot site. The proportion of dissolution agent at the clot site is further controlled to prevent or minimize injury to the blood vessel wall.

FIG. 1 shows the distal end portion of a device according to the invention composed of, in addition to, infusion catheter 2, a suction catheter 3 in position in a blood vessel 4. A principal application of the present invention is the removal of clots in coronary arteries. Catheter 2 may be tapered at its distal end 5 to facilitate insertion and advance to the site of a clot.

Catheter 2 is provided with a plurality of lumens and lateral openings which perform various functions in a clot dissolution procedure. The internal structure of catheter 2 is illustrated more fully in FIGS. 2 and 3, to which reference will now be made together with FIG. 1.

Because a separate catheter 3 is employed to perform the suction operation, the suction lumen in catheter 3 can be made larger than a suction lumen which might otherwise be provided in catheter 2.

Figure 2:
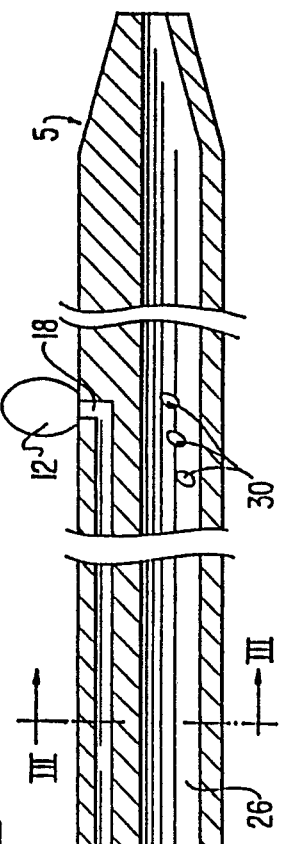
FIG. 2 is a side cross-sectional view of sections of the distal portion of one catheter of FIG. 1, to a larger scale, taken along line II—II of FIG. 3.
Figure 2:
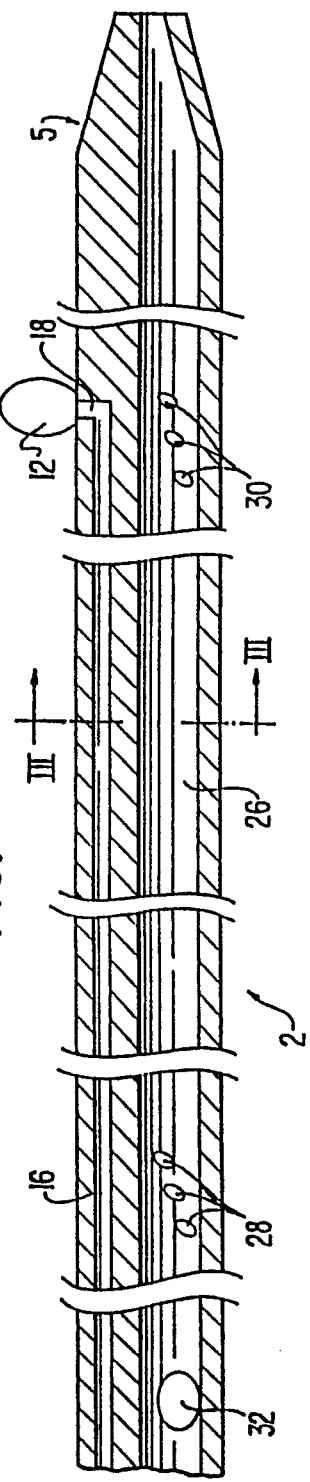

According to one embodiment of the present invention, the clot site in vessel 4 may be blocked by a balloon 12 fixed to the peripheral wall of catheter 2 and a balloon 13 fixed to the peripheral wall of catheter 3, each balloon having an inflation opening for the introduction of inflation air via a lumen and an outlet opening of its respective catheter. In FIG. 2, a lumen 16 and outlet opening 18 for balloon 12 are shown. Balloons 12 and 13 are shown in their inflated state in FIG. 1 and balloon 12 is shown in its deflated state in FIG. 2.

As is apparent from FIGS. 1 and 2, balloons are constructed such that the inflation opening of each balloon is attached to a small portion of the periphery of the associated catheter and each balloon expands eccentrically relative to the longitudinal axis of its catheter. This is particularly desirable with regard to catheter 2, which is normally inserted first, because expansion of balloon 12 will urge catheter 2 toward the wall of vessel 4 leaving a relatively large free space for insertion of catheter 3. On the other hand, balloon 13 may be eccentric, as shown, or concentric, i.e., in the form of an annular cuff.

While embodiments are conceivable in which both balloons 12 and 13 are carried by catheter 2, in which case inflation of balloon 13 would be effected via a separate lumen and outlet opening, the mounting of balloon 13 on catheter 3 offers the advantage of permitting variation of the length of the blood vessel region enclosed by the balloons.

In the case where the obstructing material is close to a branching blood vessel, as shown at 14 in FIG. 1, balloon 13 can be positioned to isolate the branching vessel from the treatment site. Alternatively, an attempt can be made to move the obstruction away from the branching vessel by displacing one of the catheters with its balloon inflated. However, it may be necessary to insert a separate balloon catheter into the branching vessel in order to block flow in that vessel.

As an alternative to a balloon, or balloons, any other known devices can be employed to obstruct blood flow downstream of the clot site, such devices including, for example, filters or sponges. Such devices should be constructed, however, to urge catheter 2 toward the wall of vessel 4.

The peripheral wall of catheter 2 is provided with two radiopaque markers 22 and 24 which are spaced apart by a distance sufficient to straddle the site of a clot. Typically, the distance between markers 22 and 24 could be of the order of 2 cm and these markers could, for example, be in the form of annular bands. Passage 10 is located essentially midway between markers 22 and 24 and balloon 12 is located between distal marker 24 and distal end 5.

When catheter 2 is properly positioned at the site of a clot and balloon 12 and/or 13 are inflated so as to block blood flow in vessel 4, it is desired to maintain a flow of blood past the clot and this is achieved, according to the present invention, by providing catheter 2 with a further lumen 26 having associated inlet openings 28 and outlet openings 30. Preferably, lumen 26 is given as large a diameter as is permitted by the available cross section of catheter 2 and the number of inlet openings 28 and outlet openings 30 is selected to provide a sufficiently low flow resistance. At the outlet end, lumen 26 extends completely to distal end 5 of catheter 2 and will serve the additional function of accommodating a guide wire during insertion of the catheter, as will be described below. However, particularly if end 5 is tapered, the outlet end of lumen 26 could present an unacceptably high flow resistance. Outlet openings 30 overcome this difficulty.

As is illustrated, openings 28 and 30 are located so that blood flowing through lumen 26 will bypass balloon 12, as well as the site of the clot, when catheter 2 is properly positioned. By way of example, the spacing between openings 28 and radiopaque marker 22 could be of the order of 4 cm. Balloon 13 will be positioned so that openings 28 will always be located to be more remote from the distal end of the catheter than is balloon 13.

Lumen 26 is further associated with a dye outlet opening 32 which is located upstream of openings 28 and via which a suitable radiopaque dye may be delivered to the clot region in order to assist X-ray observation of the positioning of catheter 2. By making opening 32 sufficiently large, dye delivered via the proximal end of lumen 26 will flow essentially entirely through opening 32, both because that opening will present a substantially lower flow resistance than will the downstream portion of lumen 26, and because the dye will be entrained in blood flowing through the vessel around catheter 2. During this time, balloon 12 is not yet inflated and either catheter 3 is not yet inserted or its balloon 13 is not inflated.

If catheter 2 is intended to be inserted into a vessel in the direction counter to blood flow, dye could be delivered via a further lumen (not shown) having outlet opening 32 disposed between distal end 5 and outlet opening 10, or a separate dye-delivery catheter could be employed.

The injection of dye or other observable agent, together with observation of its behavior in the blood vessel, allows the positioning of catheters 2 and 3 and the appropriate inflation states of balloons 12 and 13 to be determined. For example, if the dye flows off via a side branch, such as branch 14 in FIG. 1, catheter 13 may have to be displaced or a separate balloon may be required in the side branch. The direction of flow of the dye can indicate which balloon will have to be deflated to admit additional blood to the treatment site. If the dye remains in place, it may be possible to perform the treatment without inflating the balloons.

Figure 3:
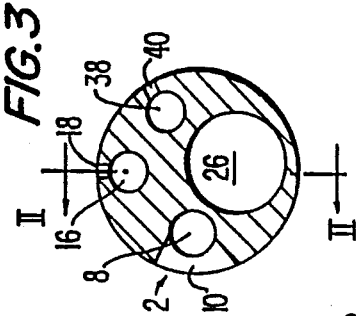
FIG. 3 is a transverse, or axial, cross-sectional view taken along the line III—III of FIG. 2.
Figure 3A:
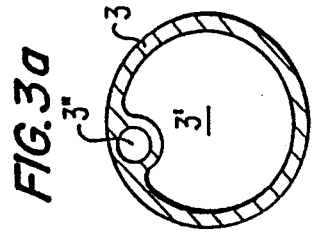
FIG. 3a is a view similar to that of FIG. 3 showing the other catheter of FIG. 1.

FIG. 3 shows, in axial cross section, one suitable arrangement of lumens in catheter 2. These can include a lumen 38 and an outlet opening 40 for delivering inflation air to balloon 13 if that balloon is carried by catheter 2. Similarly, FIG. 3a shows catheter 3 having a large area suction lumen 3' and a balloon inflation lumen 3''.

A clot removal operation according to the present invention could be carried out by the following procedure, which incorporates conventional insertion techniques. The procedure to be described by way of example is intended to remove a clot which has been found to be present in a coronary artery, and consists of the following sequence of steps:

1) A needle is inserted into the artery from outside the body, one location currently used being in the patient's groin.
2) A guide wire is inserted through the needle and into the artery to a distance possibly of the order of 10 cm.
3) The needle is then removed.
4) A sheath is slid around the guide wire and into the artery.
5) A guiding catheter is placed around the guide wire and into the sheath, the guiding catheter is advanced into the coronary artery, and the sheath is removed from the artery.
6) The guide wire is then advanced through the guiding catheter and then past the distal end of the guiding catheter and across the site of the clot.
7) The guiding catheter is then withdrawn from the artery.
8) Then, infusion catheter 2 having the form shown in FIGS. 1–3 is placed over the guide wire, i.e., lumen 26 is threaded around the guide wire and catheter 2 is advanced to the site of the clot, the position of catheter 2 being observable by the effect of X-rays on markers 22 and 24.
9) When it appears that catheter 2 is at least approximately correctly located, the guide wire may be withdrawn and a suitable dye is introduced via lumen 26 and opening 32 into the blood stream in order to allow X-ray observation of the clot and behavior of the dye and to permit final positioning of catheters 2 and 3.
10) When it is determined that catheter 2 has been properly positioned, eccentric balloon 12 is inflated in order to block one side of the region which is the site of the clot and to urge catheter 2 to one side of the artery.
11) Suction catheter 3 is then inserted and advanced to the treatment site, if necessary by a procedure as outlined at 1)-8). At this time, an attempt can be made to withdraw the clot simply by applying suction via catheter 3. After an appropriate interval, balloon 12 may be deflated and dye introduced via opening 32 to permit observation of the status of the clot.
12) If the clot is not removed in step 11), normally balloons 12 and 13 will be inflated and thrombolytic agent is introduced, via lumen 8 and opening 10, at a rate sufficient to establish a sufficient concentration thereof at the treatment site. Fluid is withdrawn from the treatment site via catheter 3 and its composition is analyzed. If the concentration of thrombolytic agent is low, the delivery rate thereof is increased, or the downstream balloon is inflated if it was previously deflated; if it is high, the delivery rate may be decreased and/or the upstream balloon is partially deflated to allow an additional quantity of blood to enter the treatment site. Suction is established, possibly after a selected dissolution time, to remove dissolved material and residual clot particles. After a selected suction period, the balloons may be deflated and additional dye introduced to observe that status of the treatment site. If necessary, the entirety of this step is repeated.

Thus, according to the invention, dissolution agent may be confined to the region between balloons and is prevented from flowing off into the remainder of the circulatory system. This means that the dissolution agent is prevented from reaching regions of the circulatory system which may, because of disease or abnormality, cause serious harm to the patient.

At the same time, the fluid composition at the clot site can be fully controlled in the manner described above.

One side of the clot site can be blocked by an eccentric balloon carried by the infusion catheter or by a separate balloon carried by the suction catheter. In the latter case, the balloon carried by the suction catheter can be moved relative to the balloon carried by the infusion catheter to adjust the length of the region blocked off by the balloons, and/or to close off a side branch adjacent the clot.

If the clot is too close to a side branch to allow the side branch to be isolated from the clot site, it may be possible to utilize the balloon which is adjacent the side branch to push the clot to a location where it can be isolated from the remainder of the circulatory system.

For the majority of applications, catheter 2 may have a size of the order of 4.5 to 7 French, a size of 5.5 French presently being preferred.

Figure 5:
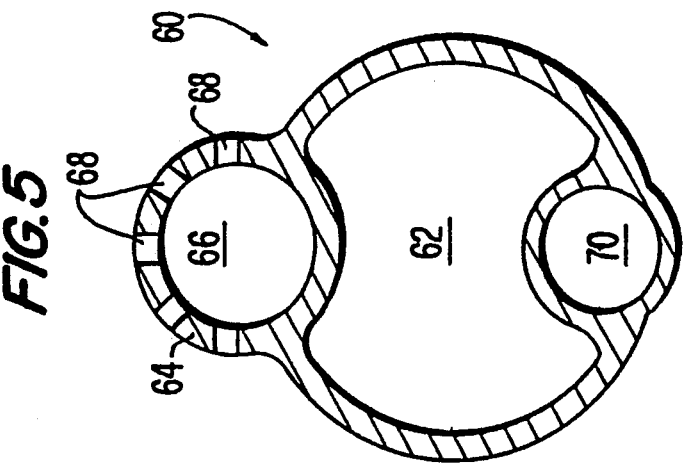
FIG. 5 is a side view, partly in cross section, of a third embodiment of a catheter according to the invention.
Figure 4:
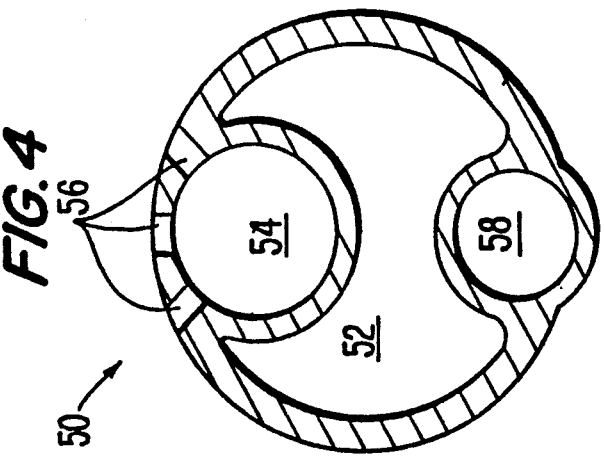
FIG. 4 is a side view, partly in cross section, of a second embodiment of a catheter according to the invention.

Two further embodiments of a catheter according to the present invention are illustrated in cross section in FIGS. 4 and 5. Each of these embodiments, like the embodiment of FIGS. 1-3, may be a unitary, extruded plastic member, the embodiments of FIGS. 4 and 5 being constructed to have a thin-walled design in order to provide relatively large flow passages. In this connection, priority should be given to the cross-sectional area of the blood bypass flow path since the maximum possible flow rate along this path can prove beneficial to the patient.

FIG. 4 illustrates a catheter 50 having a basically cylindrical form and an internal configuration which provides a lumen 52 defining a blood bypass flow path occupying substantially more than one-half of the catheter interior cross section. Along the upper portion of catheter 50, there is provided a lumen 54 defining a thrombolytic agent flow path which will communicate with the region surrounding catheter 50 via a plurality of outlet passages 56 which replace the single large opening 10 of the embodiment shown in FIGS. 1-3.

Finally, catheter 50 is provided with a balloon inflation lumen 58.

In this embodiment, the wall of lumen 58 projects radially slightly beyond the basic circular outline of catheter 50 in order to permit the cross-sectional area of lumen 52 to be enlarged.

In the embodiment shown in FIG. 5, catheter 60 is formed to have a still larger blood bypass flow lumen 62 by constructing the thin-walled structure of catheter 60 to have a radially protruding portion 64 which encloses a lumen 66 for delivering thrombolytic agent. Because of the radially protruding position of portion 64, the outlet end of lumen 66 can be provided with a number of outlet openings 68. Catheter 60 is completed by a balloon inflation lumen 70 corresponding essentially to lumen 58 of FIG. 4.

In each of the embodiments illustrated in FIGS. 4 and 5, a second balloon inflation lumen may be provided at any desired location if the catheter is to carry the second balloon 13 which is to be separately inflated. In addition, the catheters according to these embodiments can have a tapered distal end, as shown for the embodiment of FIGS. 1-3, and lumens 52 and 62 will extend the entire length of the catheter to serve the additional function of accommodating a guide wire.

Further, in the embodiments of FIGS. 4 and 5, a radiopaque dye may be delivered to the region of the clot via the blood bypass flow lumen 52, 62, in a manner similar to that described above with reference to FIGS. 1-3. Specifically, lumen 52, 62 can extend fully to the proximal end of the catheter and, at a location upstream of the blood bypass flow region, this lumen may be provided with a large opening or an array of openings via which all or substantially all of a dye introduced via the proximal end of the catheter will exit into the blood stream. When no dye is being delivered, this opening or openings may serve as additional blood bypass flow inlet openings.

Figure 6:
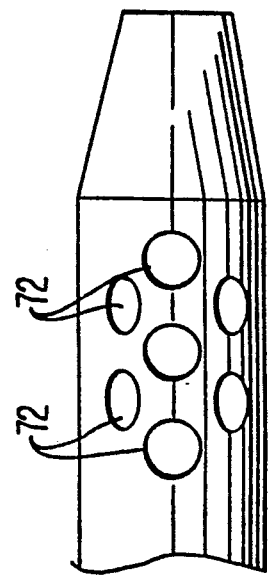
FIG. 6 is a side view of the distal end of a catheter according to the present invention.

In each embodiment of the present invention, the inlet and outlet openings for the blood bypass flow path may be constituted by an array of openings 72, as shown in FIG. 6. This array may be distributed around one-half of the circumference of the catheter or, in the embodiments of FIGS. 4 and 5, may be provided in both halves of the circumference of the catheter, outside of the regions occupied by the other lumens, 54, 58, 66, 70. Openings 56 and 68 may also be distributed to have the form of array 72.

According to a further feature of the invention, catheter 3 may be provided with a balloon 13' which, upon inflation, assumes an oblong configuration, or is elongated in the longitudinal direction, as shown in FIG. 7. Such a balloon, which can be fabricated according to principles known in the balloon fabrication art, has an enhanced capability of blocking blood vessel side branches immediately adjacent the treatment site. If balloon 13' is provided, it may be necessary to place openings 28 and 32 at a greater distance from distal end 5 of catheter 2.

Another characteristic of the embodiment of FIG. 7 is that balloon 13' is configured to expand symmetrically around catheter 3. This permits balloon 13' to effectively block side branches at any location around the circumference of vessel 4.

While a preferred embodiment of a device according to the invention has been described and illustrated, it will be appreciated that various rearrangements of the component parts can be made without departing from the spirit and concept of the invention. Thus, as already mentioned, balloon 13 or 13' could be carried by infusion catheter 2. Alternatively, catheter 2 could carry a single balloon at the location of balloon 13, instead of at the location of balloon 12, particularly if, for any reason, it is desirable or necessary to insert catheter 3 from the direction opposite to that of catheter 2.

A treatment procedure according to the invention could further include introduction of an observation device to the treatment site.

As an alternative to the embodiments described above, embodiments of the invention may include but a single eccentric balloon, preferably mounted on infusion catheter 2. This arrangement may prove preferable for dealing with certain anatomical conditions encountered in the circulatory system. Depending on the conditions existing at the treatment site, relating to the actual blood flow pattern and the nature of the obstructions in the vicinity of the treatment site, the single balloon may be either at the distal location of balloon 12 or at the proximal location of balloon 13. Such an alternative arrangement would be utilized in situations where it is still possible to satisfy the goal of maintaining the desired quantity of dissolution agent and the desired proportion of blood at the treatment site by appropriate control of the dissolution agent delivery rate and the suction rate, while substantially preventing any significant flow of the dissolution agent away from the treatment site and through the remainder of the circulatory system.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A method of dissolving an clot in a blood vessel, comprising:
    preventing blood which is in contact with the clot from flowing through the vessel to locations downstream of the clot while permitting blood to flow through a passage past the clot;
    delivering to the clot a dissolution agent which works in conjunction with blood components to effect dissolution of the clot, so that a fluid which includes the dissolution agent and blood is in contact with the obstruction;
    withdrawing a sample of the fluid, which includes portions of dissolved clot material, from the blood vessel;
    directly determining the composition of the fluid in the sample; and
    adjusting the concentration of dissolution agent in the fluid in contact with the clot on the basis of the result of said determining step.

2. A method as defined in claim 1 wherein said step of adjusting comprises supplying blood to the fluid in contact with the clot.

3. A method as defined in claim 1 wherein said step of adjusting comprises increasing the quantity of dissolution agent in he fluid in contact with the clot.

4. A method as defined in claim 1 wherein the concentration of dissolution agent in the fluid in contact with the clot has an optimum range of values, and said step of adjusting comprises supplying blood to the fluid in contact with the clot when said determining step indicates that the concentration of dissolution agent in the fluid in contact with the clot is higher than the optimum range, and increasing the quantity of dissolution agent in the fluid in contact with the clot when said determining steps indicate that the concentration of dissolution agent in the fluid in contact with the clot is lower than the optimum range.

5. A method as defined in claim 4 wherein said steps of determining and adjusting are performed a plurality of times in the recited order.

6. A method as defined in claim 1 wherein said steps of determining and adjusting are performed a plurality of times in the recited order.

* * * * *